United States Patent [19]

Braeumer et al.

[11] 4,232,123

[45] Nov. 4, 1980

[54] METHOD FOR MAKING WATER-SOLUBLE HYDROLYZATES OF KERATINACEOUS MATERIALS

[75] Inventors: Klaus Braeumer, Weinheim; Zdenek Eckmayer, Heidelberg; Alexander Berg, Holzminden; Rolf Monsheimer, Darmstadt-Eberstadt; Ernst Pfleiderer, Darmstadt-Arheilgen, all of Fed. Rep. of Germany

[73] Assignees: Firma Carl Freudenberg, Weinheim; RUM/o/ hm GmbH, Darmstadt, both of Fed. Rep. of Germany

[21] Appl. No.: 55,963

[22] Filed: Jul. 9, 1979

Related U.S. Application Data

[63] Continuation-in-part of Ser. No. 876,239, Feb. 9, 1978, abandoned.

[30] Foreign Application Priority Data

Feb. 11, 1977 [DE] Fed. Rep. of Germany ....... 2705669

[51] Int. Cl.$^3$ .................. C12P 21/06; C12P 13/12; C14C 1/00; C07G 7/00
[52] U.S. Cl. ...................... 435/69; 435/68; 435/113; 435/265; 435/272
[58] Field of Search ................. 435/265, 68, 69, 113, 435/272

[56] References Cited

U.S. PATENT DOCUMENTS

| 2,212,750 | 8/1940 | Pfannmuller et al. ............ 435/265 |
| 2,322,313 | 6/1943 | Phillips et al. ................... 435/265 |
| 2,363,646 | 11/1944 | Conquest et al. ................. 435/265 |
| 2,817,342 | 12/1957 | Henkin ........................... 435/228 X |
| 2,988,487 | 6/1961 | Nickerson et al. ............. 435/244 X |
| 2,988,488 | 6/1961 | Robison et al. .................. 435/265 |

FOREIGN PATENT DOCUMENTS

1414634  11/1975  United Kingdom.

OTHER PUBLICATIONS

D. A. Hall, "The Reaction Between Elastise and Elastic Tissue", Journal of Biochemistry, vol. 59, pp. 459–464, 1955.

Hoppe-Seyler/Thierfelder, Hardback der Physiologisch und Pathologisch–Chem Analyse, Tenth Ed., vol. II, p. 495, 1960.

A. L. Everett et al., Assay of Proteolytic Depilatory Enzymes on Keratin Activation with Metabisalfite, paper presented at Annual Meeting of Society of Amer. Bacteriologists, 1960.

*Primary Examiner*—Robert J. Warden
*Attorney, Agent, or Firm*—Curtis, Morris & Safford

[57] ABSTRACT

A method is disclosed for making a water-soluble hydrolyzate of a keratinaceous starting material which comprises first subjecting said starting material to acid treatment at a pH of 2 or below and at an elevated temperature above 80° C. to effect mild hydrolysis thereof and then enzymatically degrading said acid-treated material in an aqueous bath in the presence of urea with an alkaline proteinase having an activity optimum in a range between pH 9 and pH 13, the initial pH of the enzymatic treatment being within the pH range optimum for the enzyme employed.

8 Claims, No Drawings

METHOD FOR MAKING WATER-SOLUBLE HYDROLYZATES OF KERATINACEOUS MATERIALS

This application is a continuation-in-part of application Ser. No. 876,239 filed Feb. 9, 1978 now abandoned.

The present invention relates to a method for the preparation of water-soluble hydrolyzates from keratinaceous raw materials such as hair, wool, or the like. More in particular, the invention relates to a method for working up wastes, particularly hair wastes from the tannery or wool wastes from the textile industry, but also wastes such as scales, nails, claws, hooves, horns, and the like.

The hydrolyzates prepared according to the invention are proteins which can be used in the cosmetic field, particularly in the treatment of skin and hair.

It is known that protein hydrolyzates, particularly hydrolyzed proteins derived from collagen, can be employed as cosmetic agents. Hydrolyzed proteins are also suitable for treatment of the hair, for example in dyeing, bleaching, dressing, and the like, and large amounts of hydrolyzed protein have been used for a long time in the past for this purpose. The proteins are obtained by the degradation of collagen-containing material, particularly by chemical (alkaline or acid) hydrolysis.

The effect of proteins consists in particular in their functioning as protective colloids for hair. The protective colloids inhibit damage which arises from oxidative influences, for example from bleaches, and from reducing permanent wave agents. Under the influence of the hydrolyzates, the suppleness and strength of the hair improves, splitting of the hair ends is avoided, and the hair acquires increased luster, a full appearance, and a pleasant hand. Simultaneously, the scalp is favorably influenced by treatment with protein hydrolyzates and the improved condition of the skin further causes a quicker growth of the hair because of the added basic materials for protein synthesis.

Numerous preparations which contain protein hydrolyzates are already commercially available. However, the action of these preparations is diverse. A certain effect is always present, although it is very variable even in the same preparation and is difficulty reproducible. The known products for this reason achieve results which are more or less widely distant from the favorable influence on hair and scalp which is theoretically conceivable.

The relatively small degree of effect of the known products is attributable, among other reasons, to the fact that the molecular weights of the degradation products vary strongly because it is not possible to achieve reproducible molecular weights by chemical hydrolysis. In addition to degradation products having the optimum molecular weight, products having lower and higher molecular weights are always formed so that the total effect is reduced. Also, the amino acid composition is not ideal for medicinal cosmetics. Certain amino acids which are typical for keratin, for example cystein and cystine, are completely absent, whereas other important amino acids, for example, tyrosine, are present in only very small amounts. Without cystein and cystine, however, the growth of hair cannot effectively be promoted.

It is an object of the invention to develop a method for the preparation of water-soluble hydrolyzates which have the amino acid composition recognized as important and the molecular weight of which can be controlled in a reproducible fashion. In this manner, products are to be prepared which contain the protein components recognized as valuable and which are all present in hair and, further, which contain them in an optimum molecular size.

A process is proposed which proceeds using keratinaceous waste products substantially free of collagenaceous material such as skin, particularly fibrous products such as loose hair or wool, wherein the waste products employed as raw materials are subjected to an acid treatment at an elevated temperature, as a rule above 80° C., and at a pH value not significantly exceeding 2, preferably less than 2, whereby a mild hydrolysis occurs. The process subsequently involves an enzymatic hydrolysis carried out in the presence of urea using alkaline proteinases having an optimum activity between pH 9 and pH 13. The hydrolysis initially proceeds in the optimum pH range for the enzyme employed. Usually, the pH value drops to 7 to 9 during the enzymatic hydrolysis. After the degradation is concluded, any enzyme which may still be present can be inactivated, as a rule by warming.

In the enzymatic treatment, the amount of enzyme employed is such as has an activity from 1000 to 20,000 Loehlein-Volhard units (LVU) per kilogram of dry substrate to be treated. The proteolytic efficacy of enzymes is determined in a known way according to the Anson hemoglobin method [M. L. Anson "J. Gen. Physiology" 22, 79 (1939)] or according to the Loehlein-Volhard method ["Die Loehlein-Volhard'sche Methode zur Bestimmung der proteolytischen Aktivitat", in the Gerbereichemisches Taschenbuch, Dresden-Leipzig (1955)]. A Loehlein-Volhard unit (LVU) is that amount of enzyme which, under the specific conditions of the method, digests 1.727 mg of casein.

Urea is employed in a weight ratio to the enzyme from 2:1 to 10:1, preferably from 2.5:1 to 5:1. The process is suitably carried out at a urea concentration between about 0.001 and 1.0 mol per liter and is carried out in the presence of alkaline proteinases from Bacillus strains such as *Bacillus licheniformis, Bacillus alcalophilus, Bacillus subtilis, Bacillus mesentericus,* or *Bacillus firmus,* and/or proteinases obtained from Streptomyces such as *Streptomyces griseus.*

The mild hydrolysis carried out before the enzymatic degradation should suitably take place over a time span of several hours, as a rule of at least 4 hours. As acids for establishing the low pH, mineral acids such as hydrochloric acid, sulfuric acid, phosphoric acid, and the like are suitable. The pH value in the treatment suitably is below 2.

Whereas the enzyme-free acid hydrolysis as a rule is carried out at temperatures of about 80° C., the temperature during the enzymatic degradation is between about 30° C. and 70° C., preferably between about 40° C. and 65° C. The inactivation of any enzymes still present after conclusion of the degradation can follow at temperatures between about 80° C. and 100° C.

The process according to the invention permits the working up of wastes which previously could not be put to any economic use. In particular, these are loose waste hair arising in tanning and loose waste wool from the textile industry.

In tanning, hair is, as is known, combined with alkali during the course of the tanning process. It is of course possible to obtain soluble products by a very strongly alkaline degradation, which products are still always of high molecular weight but which are amenable to enzymatic attack. Such products are not the object of the present invention, since an enzymatic degradation of tannery hair has serious disadvantages if the degradation products are to be used, for example in the cosmetic industry. Thus, the solution so obtained contains large amounts of undesirable mineral materials. Because of the strongly alkaline degradation, the toxic products lanthionine and lysino-alanine are also formed. It is understandable that, for these reasons, the degradation products are unsuitable for use in hair cosmetology or are damaging.

For the reasons set out above, it is essential to carry out the enzymatic degradation according to the manner of the present invention. In this case, the hair, detached from the skin or hide, is separated from the tanning process before there is too strong damage thereto by alkali. The hair is, to be sure, already slightly alkali-damaged, however it is still insoluble because its structure has been retained. In this condition, the hair is not susceptible to enzymatic attack and must be subjected to a mild hydrolysis by acid treatment, according to the teachings of the present invention, before the actual enzymatic degradation. For this purpose, the loose hair wastes are filtered from alkaline solution, neutralized with dilute acid, and freed of mineral salts by repeated washing. The now-clean loose hair serves as a starting product for the process according to the present invention, which comprises a hydrolytic and enzymatic degradation.

Loose wastes from the wool industry, also detached from any collagenaceous substrate, are easier to prepare. They are freed of dust by washing and can be used directly in this condition as a raw material according to the process of the present invention.

The raw materials prepared in the manner described above are now acid-hydrolyzed at pH values preferably below 2 and at an elevated temperature above 80° C. In order to avoid the production of toxic products, there must be no alkaline treatment. For this reason, the raw material is exclusively treated with acid. It remains water-insoluble after such treatment.

The acidification of the raw material is carried out with mineral acids, for example, sulfuric acid. At a pH value beneath 2, the sulfide bridges of the acidified material are cleaved on cooking for several hours, at least for about two hours. The material is in this way made amenable to a subsequent enzyme treatment. The enzymatic degradation then follows without difficulty. The degradation products correspond extensively with the starting products in their amino acid composition, whereby it is demonstrated that the important components of the hair are not destroyed.

For the subsequent enzymatic liquefaction in the alkaline region, proteinases from Bacillus strains or Streptomyces species such as those mentioned earlier herein are particularly suitable. Enzymes which cleave in the acid region are less suitable for the process according to the present invention because degradation proceeds too slowly. Thus their technical utilization, as a rule, fails.

For establishing an alkaline condition, the bases usually employed in enzymatic reactions, particularly ammonia, are used. Other suitable bases include alkali metal and alkaline earth metal hydroxides such as sodium hydroxide, potassium hydroxide, and calcium hydroxide.

It is possible, by a suitable choice of the enzyme (and hence of pH), of the enzyme concentration, and of the treatment time and temperature to influence the degree of degradation of the product in a reproducible manner. According to the conditions chosen for the enzymatic degradation, keratin hydrolyzates having short chains or intermediate chains can be prepared. If a conversion into modified protein derivatives is desired, it is suitable to carry out the degradation to form short-chain hydrolyzates having molecular weights of about 1000. Keratin hydrolyzates having molecular weights between 1000 and 8000, particularly from 1000 to 5000, have particularly good properties for use in cosmetic products. The reaction can also be used to give products having molecular weights up to about 20000, which latter are useful as nutrients, for example in animal feed.

In practise, under the conditions of pH, temperature, amount of enzyme, etc. already discussed, treatment times in the enzymatic hydrolysis step are as a practical matter not less than 4 hours and not more than 24 hours, after which decomposition begins.

In many cases, it is suitable to improve the acid, enzyme-free treatment by the addition of an oxidizing agent, for example a 0.5 percent hydrogen peroxide solution, to the acidified hair before cooking. In this way, the treatment time for the acid treatment can often be considerably shortened.

The hydrolyzate solution is optionally freed of impurities and by-products by filtration and is then reduced to the desired concentration. It can also be dried to form a powder. The hydrolyzate has a good effect which clearly is greater than the effect of known keratin proteins. Basically, the hydrolyzate can be used in all fields of use which are known for protein hydrolyzates.

A better understanding of the present invention and of its many advantages will be had by referring to the following specific Examples, given by way of illustration.

EXAMPLE 1

100 kg of limed hair mixture from tannery production, detached from the skin or hide, are introduced into a container equipped with a stirrer. The pH value of the mixture is about 12. By the addition of dilute hydrochloric acid, the pH value is reduced with good mixing to 7.0. The mixture is then squeezed out and washed several times with distilled water, whereby the filter residue after each washing is squeezed out again. The last washing is carried out with water warmed to 70° C.

20 kg of damp squeezed-out hair cleaned in the manner described above are introduced into a heating vessel and the pH value of the mixture is adjusted to 2 with sulfuric acid. The mixture is cooked for six hours. Subsequently, the hair is washed out several times with distilled water and is squeezed out.

The subsequent enzymatic decomposition of the hair treated in the manner described above follows in a heating vessel upon the addition of 80 liters of distilled water. The mixture is adjusted to an initial pH value of 9.5 with ammonia, warmed to 50° C., and 10 g (9000 LVU per gram) of alkaline bacterial proteinase derived from *Bacillus licheniformis* and having optimum activity at pH 9.3–10.8, 40 g of urea, and 50 g of ammonium sulfate (an inert carrier which may be omitted or replaced by some other inert carrier salt such as sodium sulfate) are added. The mixture is maintained for ten hours at 50° C. for decomposition. During this time, the hair dissolves almost completely. After decomposition, the material is heated to 95° C. in order to destroy any enzyme which might still be present and is then cooled.

The decomposed material is prefiltered through a cloth and subsequently centrifuged once. Subsequently, a further filtration follows through a filter layer. The yield after filtration amounts to 80 liters of a dark-colored liquid having a solids content (dry weight) of 9.4 percent and a pH value of 9.5. The liquid is adjusted to a pH value of 7.0 and is spray dried. Another portion is concentrated to about 35 percent by weight. The average molecular weight of the hydrolyzate is about 3,500.

EXAMPLE 2

65 l of distilled water are introduced together with pre-cleaned loose wool (dry weight=4.5 kg into a heatable container. The material is adjusted to a pH value of 1.5 by the addition of sulfuric acid and is cooked for eight hours. After cooking, the wool is cooled, washed with distilled water, and squeezed out.

The cleaned wool is introduced into a heating kettle with 95 liters of water and is warmed to 55° C. as in Example 1. Using ammonia, the pH value is adjusted to 9.3 and, subsequently, 4.0 g (7000 LVU per gram) of bacterial proteinase derived from *Bacillus subtilis* and having optimum activity at pH 9.2–11.0, 18 g of urea, and 23 of ammonium sulfate (an optional inert carrier salt) are added. The mixture remains for 20 hours at this temperature and is stirred now and then. The pH value at the end of the hydrolysis is 7.8. Subsequently, the solution is heated to 95° C. After cooling to about 40° C., filtration through a filter layer and subsequent spray drying follow. The yield is 3.6 g of a powder having a dry weight of 96.9 percent. The average molecular weight of the hydrolyzate is about 1,000.

Similar processes can be used to treat keratinaceous wastes, substantially free of collagenaceous materials, such as scales, nails, claws, hooves, horns, and the like.

What is claimed is:

1. A method for making a water-soluble hydrolyzate of keratinaceous starting material, wherein the keratinaceous starting material is selected from the group consisting of loose hair, loose wool, scales, nails, claws, hooves and horns, which method comprises first subjecting said starting material to acid treatment in a treating bath at a pH of 2 or below and at an elevated temperature above 80° C. to effect mild hydrolysis thereof and then enzymatically degrading said acid-treated material in an aqueous bath at a temperature between about 30° C. and 70° C. for 4 hours to 24 hours in the presence of urea with an alkaline bacterial proteinase having an activity optimum in a range between pH 9 and pH 13, the initial pH of the enzymatic treatment being within the pH range optimum for the enzyme employed.

2. A method as in claim 1 wherein any enzymes present at the conclusion of the enzymatic degradation are subsequently inactivated.

3. A method as in claim 1 wherein said acid treatment is at a pH below 2.

4. A method as in claim 3 wherein said acid treatment is carried out at the boiling point of the treating bath.

5. A method as in claim 1 wherein the urea concentration in said aqueous bath is between about 0.001 mol per liter and 1.0 mol per liter.

6. A method as in claim 1 wherein said alkaline bacterial proteinase is derived from a Bacillus strain or from a Streptomyces species.

7. A method as in claim 1 wherein said member is loose hair.

8. A method as in claim 1 wherein said member is loose wool.

* * * * *

UNITED STATES PATENT AND TRADEMARK OFFICE
CERTIFICATE OF CORRECTION

PATENT NO. : 4,232,123

DATED : November 4, 1980

INVENTOR(S) : Klaus Braeumer et al.

It is certified that error appears in the above-identified patent and that said Letters Patent are hereby corrected as shown below:

On the Title page Item [73] Assignee should read:

Firma Carl Freudenberg, Weinheim;
    Röhm GmbH, Darmstadt,
    both in the Federal Republic of Germany.

On the cover page, right-hand column:

in line 7, replace "Elastise" by --Elastase--;
    in line 10, replace "Hardback" by --Handbuch--;
    in line 14, replace "Metabisalfite" by --Metabisulfite--.

Signed and Sealed this

Twenty-fourth Day of August 1982

[SEAL]

*Attest:*

*Attesting Officer*

GERALD J. MOSSINGHOFF

*Commissioner of Patents and Trademarks*